(12) United States Patent
Stankov (10) Patent No.: US 9,140,700 B2
(45) Date of Patent: Sep. 22, 2015

(54) DEVICE FOR DETERMINING AT LEAST ONE ANALYTE CAPABLE OF BEING CONTAINED IN A LIQUID SAMPLE

(71) Applicant: Milovan Stankov, Plesse (FR)

(72) Inventor: Milovan Stankov, Plesse (FR)

( * ) Notice: Subject to any disclaimer, the term of this patent is extended or adjusted under 35 U.S.C. 154(b) by 0 days.

(21) Appl. No.: 14/382,809

(22) PCT Filed: Mar. 19, 2013

(86) PCT No.: PCT/FR2013/050588
§ 371 (c)(1),
(2) Date: Sep. 4, 2014

(87) PCT Pub. No.: WO2013/140089
PCT Pub. Date: Sep. 26, 2013

(65) Prior Publication Data
US 2015/0168397 A1      Jun. 18, 2015

Related U.S. Application Data

(60) Provisional application No. 61/612,564, filed on Mar. 19, 2012.

(30) Foreign Application Priority Data

Oct. 24, 2012    (FR) ..................................... 12 60120

(51) Int. Cl.
*G01N 21/75* (2006.01)
*G01N 33/558* (2006.01)
*G01N 33/76* (2006.01)
*G01N 33/543* (2006.01)
*G01N 21/64* (2006.01)
*G01N 21/77* (2006.01)

(Continued)

(52) U.S. Cl.
CPC ........ *G01N 33/558* (2013.01); *G01N 33/54393* (2013.01); *G01N 33/76* (2013.01);

(Continued)

(58) Field of Classification Search
CPC .................. G01N 33/54386; G01N 2021/752; G01N 21/78; G01N 21/8483; G01N 2021/6439; G01N 2021/757; G01N 2021/7793; G01N 2430/00; G01N 33/558; G01N 33/76; G01N 33/54393; B01L 2200/16; B01L 2300/0816; B01L 2400/0406; B01L 2300/0825

See application file for complete search history.

(56) References Cited

U.S. PATENT DOCUMENTS

| 5,602,040 | A  | 2/1997 | May et al. |
| 6,187,598 | B1 | 2/2001 | May et al. |

(Continued)

FOREIGN PATENT DOCUMENTS

| EP | 0 291 194 | 11/1988 |
| EP | 0 560 410 | 9/1993 |

(Continued)

OTHER PUBLICATIONS

International Search Report dated Jun. 6, 2013, corresponding to PCT/FR2013/050588.

*Primary Examiner* — Dennis M White
(74) *Attorney, Agent, or Firm* — Young & Thompson (57) ABSTRACT

A device for determining the presence and/or amount of at least one analyte contained in a liquid sample, includes a capillary diffusion element (2) materialized on which are a zone (3) for depositing the liquid sample, an upstream release zone (4) and at least two capture zones (5). The device (1) also includes at least one downstream release zone (6) located downstream of at least one of the capture zones, which downstream release zone (6) includes at least one detection reagent conjugated to a visible and/or measurable marker; and the detection reagent of a release zone and/or the capture reagent of the additional capture zone(s), located directly downstream of the release zone, are suitable for binding specifically with the analyte and/or for binding specifically with one another, in order to form a complex that enables the determination of the analyte in the liquid sample at the additional capture zone(s).

16 Claims, 2 Drawing Sheets

(51) Int. Cl.
*G01N 21/84* (2006.01)
*G01N 21/78* (2006.01)

(52) U.S. Cl.
CPC ..... *B01L 2200/16* (2013.01); *B01L 2300/0816* (2013.01); *B01L 2300/0825* (2013.01); *B01L 2400/0406* (2013.01); *G01N 21/78* (2013.01); *G01N 21/8483* (2013.01); *G01N 33/54386* (2013.01); *G01N 2021/6439* (2013.01); *G01N 2021/752* (2013.01); *G01N 2021/757* (2013.01); *G01N 2021/7793* (2013.01); *G01N 2430/00* (2013.01)

(56) References Cited

U.S. PATENT DOCUMENTS

| | | | |
|---|---|---|---|
| 6,228,660 | B1 | 5/2001 | May et al. |
| 6,818,455 | B2 | 11/2004 | May et al. |
| 7,109,042 | B2 | 9/2006 | May et al. |
| 2001/0008774 | A1 | 7/2001 | May et al. |
| 2001/0041368 | A1 | 11/2001 | May et al. |
| 2005/0244986 | A1 | 11/2005 | May et al. |
| 2006/0199278 | A1 | 9/2006 | Leclipteux et al. |
| 2007/0042504 | A1 | 2/2007 | Yu |
| 2010/0120017 | A1 | 5/2010 | Badwan et al. |

FOREIGN PATENT DOCUMENTS

| | | |
|---|---|---|
| EP | 0 560 411 | 9/1993 |
| EP | 1 091 808 | 7/2003 |
| EP | 1 657 550 | 5/2006 |
| EP | 1 933 139 | 6/2008 |
| WO | 98/22800 | 5/1998 |
| WO | 00/00288 | 1/2000 |
| WO | 2007/023372 | 3/2007 |

DEVICE FOR DETERMINING AT LEAST ONE ANALYTE CAPABLE OF BEING CONTAINED IN A LIQUID SAMPLE

FIELD OF THE INVENTION

The present invention relates to a device for determining at least one analyte capable of being contained in a liquid sample.

The invention relates in particular to the devices implementing an immunochromatographic technique by lateral migration.

BACKGROUND ART

Most of the techniques for determining analyte(s) have gradually evolved into devices which are increasingly simple to use, allowing the development of rapid and low cost routine diagnostic methods.

This change was particularly significant in the medical field, with the emergence of the diagnostic by "point of care" or "home testing", in which a diagnostic is directly carried out next the patient bed or at home, without the need for using analytical laboratory automated techniques.

Immunoassays are Part of the Technologies Used for this Type of Rapid Diagnostic.

These immunoassays encompass devices and methods of diagnostic based on affinity binding reactions between specific binding pair members.

Globally, these immunoassays are divided into two well known main approaches.

In the so-called "competition" approach, the desired analyte and a labeled detection reagent are in competition for specifically binding to a capture reagent. The presence or the absence of the desired analyte in the sample is measured, respectively, by the absence or the presence of a visible (or measurable) signal at the capture reagent.

In the so-called "sandwich" approach, a labeled detection reagent binds to the desired analyte, the latter being immobilized on the solid support via the capture reagent. The presence or the absence of the analyte in the liquid sample is measured, respectively, by the presence or the absence of a visible (or measurable) signal at the capture reagent.

Among these immunoassays, the so-called "immunochromatographic" devices which particularly lend to certain analytes are known.

The immunochromatography consists in a solid phase diagnostic method, using dry chemistry and lateral migration on an inert membrane.

This kind of immunoassay implements a porous support in a strip form, in which and/or on which are inserted in a dry form the reagents required for performing the test.

The porous support is treated so that a recognition reaction between specific binding partners (generally antigen/antibody) occurs at a capture zone and can be revealed at this level.

In practice, when the liquid sample to be analyzed is deposited on the support, the same migrates along the membrane by a capillary action. The desired analyte is generally captured by a specific capture reagent immobilized on a given zone of the membrane.

The reaction is revealed by a labeled specific detection reagent according to the sandwich method principle.

It is also possible to use a competition type reaction. Generally in this case is used a detection reagent consisting in a labeled analyte which is competitor of the desired analyte for the specific binding with the immobilized capture reagent.

These immunochromatographic devices are generally suitable for a single and domestic use. Indeed, they are of easy and rapid use, requiring only minimal handling since all of the reagents are inserted or comprised in the device.

However, in some particular situations, these immunochromatographic devices are capable of providing results that are not fully reliable.

On one hand, when determining an analyte by a "sandwich" format test, a "hook effect" is observed for certain analytes.

The hook effect is an unwanted effect well known in immunological tests. It occurs when the analyte is present in the sample at a very high concentration.

The hook effect can then result in false negatives, leading to the aberrant conclusion that there is no analyte or it is present at a low concentration in the sample.

Analytes having a hook effect in sandwich type immunoassays generate signal/concentration curves of the Gauss curve type.

For a given signal, two concentrations are then possible, one being low and the other high, for the desired analyte when reading the result at a defined time.

A competition test allows for two different signals to be obtained for two concentrations respectively different from the analyte to be dosed.

But very rapidly, the competition tests also show their limitations, since there is signal extinction at relatively low concentrations of the analyte of interest.

A solution commonly adopted to overcome the drawbacks of these sandwich and competition tests consists in dosing the analyte from a dilution range of the liquid sample.

But the use of such a dilution range is not suitable for domestic use. Furthermore, the use of a dilution range of the sample requires additional handlings and an increased consumption of single use test devices because each sample is tested at the different dilutions.

A solution for that purpose is for example described in WO 2007/023372, relating to a device for determining an analyte in a liquid sample, comprising a capillary diffusion means on which are materialized:

a) a sample depositing or receiving zone;

b) an upstream release zone comprising an analyte-specific detection reagent conjugated to a visible and/or measurable marker, which is free to migrate by capillary diffusion in a wet state in the capillary diffusion means; and c) two downstream capture zones comprising, successively in the capillary diffusion direction, on one hand, an analyte-specific capture reagent and, on the other hand, the analyte or an analogue of the analyte, which is immobilized.

The detection reagent and the capture reagent, specific of the analyte, allow for the determination of the analyte in the liquid sample by a sandwich test; then the same analyte-specific detection reagent and the analyte, or the analyte analogue, immobilized, allow for the determination of the analyte of interest in the liquid sample by a competition test.

In such a device, the detection reagent is deposited in excess at a single release zone which is formed upstream of the complementary capture zones.

Despite of its interest, the inventors found that this excess of detection reagent upstream of the capture zones is not satisfactory, in that non specific reactions, a strong background and migration problems are frequently observed.

On the other hand, certain immunochromatographic devices are structured for the simultaneous determination of several analytes.

Such an immunochromatographic device, for example, described in EP-1 657 550, comprises advantageously a capillary diffusion means on which are materialized:
  a) a sample depositing or receiving zone;
  b) an upstream release zone comprising a mixture of detection reagents, each specific of one of the analytes, conjugated to a visible and/or measurable marker, which are free to migrate by capillary diffusion in a wet state in the capillary diffusion means; and
  c) downstream capture zones each comprising a capture reagent which is specific of one of the analytes, said downstream capture zones being distributed successively according to the direction of migration.

Again, the detection reagents are deposited at the single release zone which is materialized upstream of the capture zones, taking into account the capillary migration direction.

However, the inventors found again that this mixture of detection reagents, upstream of the different capture zones, is not satisfactory because of cross reactions between the different detection reagents and also mutual specific activity inhibition between reagents.

Immunochromatographic devices comprising a release zone of the detection reagent(s), which is formed upstream of a plurality of capture zones, are not thus satisfactory.

There is therefore a need for new capillary diffusion determination devices both for the determination of a single analyte and for the determination of several analytes, allowing to alleviate the problems generated especially by the excess and/or the mixture of detection reagent(s) reported upstream of a plurality of successive capture zones.

SUMMARY OF THE INVENTION

The present invention thus relates a device for determining the presence and/or the amount of at least one analyte capable of being contained in a liquid sample, comprising a capillary diffusion means on which said liquid sample is intended to migrate laterally according to a direction and a way of capillary migration.

Various zones are materialized on this capillary diffusion means, in said capillary migration direction upstream to downstream, namely at least:
  one zone for depositing the liquid sample,
  one upstream release zone which comprises at least one detection reagent conjugated to a visible and/or measurable marker, said detection reagent being capable to move as a consequence of the migration of the liquid sample in said capillary diffusion means, and
  at least two capture zones which comprise each at least one capture reagent immobilized on said capillary diffusion means.

This device further includes at least one downstream release zone which is materialized on said capillary diffusion means and which is located downstream of at least one of said capture zones.

This downstream release zone comprises also at least one detection reagent conjugated to a visible and/or measurable marker, said detection reagent being capable to move as a consequence of the migration of the liquid sample in said capillary diffusion means.

The detection reagent of a release zone and/or the capture reagent of the complementary capture zone(s), located directly downstream of said release zone, are then capable of specifically binding to said analyte and/or specifically binding to each other to form a complex allowing the determination of said analyte in said liquid sample at said complementary capture zone(s).

Generally, such an arrangement has particularly the interest of allowing an adaptation, in quantity and/or specificity, of the detection reagent of a release zone depending on the capture reagent constituting the capture zone(s) located directly downstream of said release zone.

Other advantageous features which may be taken in combination or independently of one another are developed below:
  the downstream release zone(s) are each inserted between two capture zones;
  an upstream group of zones comprises an upstream capture zone located directly downstream of the upstream release zone, advantageously suitable for a sandwich-format test, which upstream group of zones is itself followed by one or more groups of zones each comprising a release zone and one or more complementary capture zones; this feature allows to optimize the concentration and specificity of the group(s) of downstream zones according to the detection thresholds of the analyte(s) to be determined.

For the determination of a single analyte, the detection reagent(s) of the release zones and/or the capture reagent(s) of the capture zones are advantageously capable of specifically binding to said analyte.

In this case, the release zones include preferably one or more detection reagents identical to each other, and the capture zones include preferably one or more capture reagents identical to each other.

Further in this case, the capillary diffusion means includes advantageously:
  the upstream release zone,
  a first capture zone or two first capture zones, complementary to said upstream release zone, and then
  either
  a downstream release zone, and
  at least two second capture zones, complementary to said downstream release zone,
  or at least two successive couples of zones each comprising:
  a release zone, and
  at least one capture zone, complementary to said related release zone.

For the detection of at least two analytes, the detection reagent of a release zone and/or the capture reagent of the complementary capture zone(s), immediately downstream of said release zone, are advantageously capable of specifically binding to one of said analytes.

According to still other advantageous features which may be taken in combination or independently of one another:
  the number of downstream release zone materialized on the capillary diffusion means, each inserted between two capture zones, is from 1 to 4, for example 2, for a standard capillary support format of 25 mm;
  the number of capture zone materialized on the capillary diffusion mean, complementary to one of the release zones located directly upstream, is from 1 to 10, preferably 5, for a standard capillary support format of 25 mm;
  the detection reagent of at least one of the release zones and the capture reagent of the complementary capture zone or one of them are capable of specifically binding to the analyte or at least one of the analytes to constitute a sandwich format test;
  the detection reagent of at least one of the release zones and the capture reagent of the complementary capture zone or at least one of them consist, in one case, in an analogue of the analyte to be determined and, in the other case, in a reagent capable of specifically binding to said analyte or to said analogue of the analyte, to constitute a competition format test;

the zone for depositing the liquid sample is (i) merged with the upstream release zone or (ii) located upstream of the upstream release zone.

The present invention further relates a process for the quantitative determination of an analyte in a liquid sample deposited on a determination device, this process comprises the following successive steps:

a step of measuring the signal strength (intensity) at each capture zone, in each zone group, a step of adding said strengths which are measured, a step of calculating a strength ratio corresponding to the added strengths for one zone group compared to the added strengths for another zone group, and a step of associating said calculated strength ratio to a quantitative value of the analyte in said liquid sample taking into account a standard curve corresponding to the strength ratio calculated on the basis of an analyte amount in said liquid sample.

FIGURES

The present invention will be further illustrated, but in any way is not limited, by the following description of various devices in accordance with the invention, this in connection with the appended drawings in which.

DETAILED DESCRIPTION OF THE INVENTION

The present invention thus relates to a device for determining at least one analyte capable of being contained in a liquid sample.

The general structure of this device according of the invention is illustrated very schematically through the various embodiments showed in the aforementioned FIGS. 1 to 5.

Generally, the reference numbers being used are retained to denote the same or similar structural elements when describing the various embodiments.

As shown in FIGS. 1 to 5, each device 1 includes a capillary diffusion means 2 on which said liquid sample (not shown) is intended to be deposited, and then to migrate laterally in an upstream to downstream capillary migration direction and sense.

Figure 1:
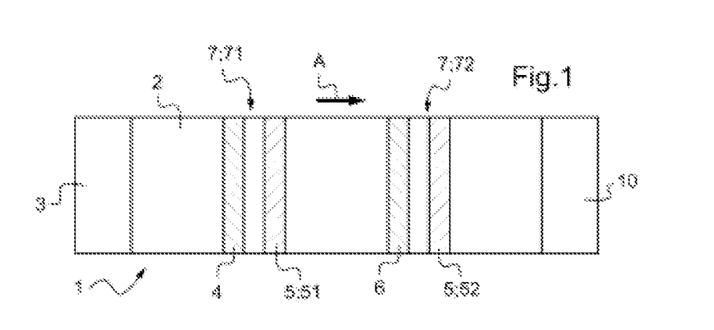
FIG. 1 depicts schematically a first device according to the invention for the determination of a single analyte, comprising two zone groups each consisting of a release zone and a capture zone.

The migration direction and sense are schematically illustrated by the arrow denoted by point A in the FIG. 1.

Generally, the notions of "upstream" and "downstream" refer to this direction and sense of migration of the liquid sample along the length of the capillary diffusion means 2.

Different successive zones are materialized on this capillary diffusion means 2 in said upstream to downstream capillary migration sense A, namely at least:

one zone 3 for depositing the liquid sample, one upstream release zone 4 which comprises at least one detection reagent conjugated to a visible and/or measurable marker, said detection reagent being able to move as a consequence of the migration of the liquid sample in said capillary diffusion means 2, and at least two capture zones 5, each comprising at least one capture reagent immobilized on said capillary diffusion means.

According to the invention, this device 1 further comprises at least one additional release zone 6 which is materialized on said capillary diffusion means 2 and which is located downstream of at least one of said capture zones 5.

This additional downstream release zone 6 also comprises at least one detection reagent conjugated to a visible and/or measurable marker, said detection reagent being able to move as a consequence of the migration of the liquid sample in the capillary diffusion means.

The capillary diffusion medium 2 thus includes several successive groups of zones 7 which each consisting of at least two successive zones:

one release zone 4 or 6, upstream, and one or more capture zones 5, called "complementary", located directly downstream of said related release zone 4, 6.

The detection reagent of a release zone 4, 6 and/or the capture reagent of the complementary capture zone(s) 5 are selected to specifically bind to said analyte and/or to each other.

This approach ensures the formation of complex(es) allowing the determination of said analyte in said liquid sample at said complementary capture zone(s) 5.

The detection and capture reagents of each group of zones 7 are in particular selected for the implementation of immunological tests in the sandwich format and/or competition format.

The presence of additional release zone(s) 6 thus allows for an optimal distribution of the detection reagents(s) within each zone group 7, which then may be arranged in a way relative to the different related capture zones 5.

So, the detection reagent within each release zone 4, 6 can be adjusted in amount and specificity relative to the complementary capture zone(s) 5, located directly downstream.

Generally, the device according to the present invention allows for the determination of analyte(s) both in low concentration and a very high concentration in a liquid sample without obtaining false positive or false negative results.

Furthermore, the device according to the invention can be structured for the semi-quantitative assay of one or more analytes in a liquid sample.

The device according to the invention is particularly suitable for the assay of analytes having a significant hook effect such as pregnancy hormone (hCG), Prostate-Specific Antigen (PSA) and hemoglobin (for example for hemoglobin detection in the stool, also called "Fecal Occult Blood" (FOB).

The other benefits of the invention related to the presence of several release zones include:
- an optimization of the detection reagents and capture reagents depending on the target concentrations to be detected,
- a higher level of accuracy.

As a consequence of the above two points, there is obtained an increase of the sensitivity and the specificity of the determination device, as well as of the interpretation value of the visible and measurable signal.

The different aspects of the present invention are shown in more details below.

Analyte(s) and Liquid Sample

By "analyte", it is meant any chemical, biochemical or biological entity that is to be detected in a sample.

This chemical entity consists advantageously in an entity from the living world, preferably, from the vegetable or animal world, more preferably, present in the human being.

Among the analytes detected by the devices and the processes according to the present invention, mention may be made in particular of proteins, peptides, antibodies, hormones, steroids, antigens derived form infectious agents or tumor cells, infectious agents such as bacteria, viruses or parasites, nucleic acids (DNA or RNA), therapeutic compounds, drugs or antibiotics.

The analyte is especially selected from those known to generate a hook effect during their detection by immunochromatographic technique.

By "hook effect", it is meant in particular a false negative result obtained by immunochromatographic technique, concluding aberrantly to the absence of the analyte in the sample, occurring when the analyte is present in the sample at a very high concentration.

Generally, the hook effect causes a weakening of the visible and measurable response signal, inversely to the increase of the analyte concentration to be determined, resulting in (i) an identical signal (of the same strength) for two different concentrations, one of which low and the other high, and (ii) an inhibition of the signal revealing for an extremely high analyte concentration.

For example, in most of the immunochromatographic tests for hCG hormone, the hook effect starts at around 5 000 mIU/mL ant should continue until about 250 000 mIU/mL, involving an identical signal strength especially for a low (25 mIU/mL) and high (200 000 mIU/mL) concentration.

In this regard, the analyte is thus advantageously selected from chorionic gonadotropic hormone (hCG), prostate-specific antigen (PSA), hemoglobin, fecal occult blood (FOB), oncogenic markers (such as ferritine, alfa feto-protein (AFP), CA15-3/CA27.29 (breast cancer), CA19-9 (pancreatic cancer), CA-125 (ovarian cancer)), C reactive protein (CRP), troponin I (TNI), cardiac markers (such as troponin T, CK-MB, myoglobin, B-type natriuretic peptide (t-BNP)), drugs of abuse (DOA), therapy monitoring biomarkers, tumor necrosis factor (TNF-alfa), other therapies associated with circulating oncogenic biomarkers, other cellular, intracellular or tissue-specific biomarkers, etc.), luteinizing hormone (LH) or follicle-stimulating hormone (FSH).

Depending on their structure, the devices according to the present invention enable the determination of a single analyte (mono-analyte) or the determination of several analytes (poly- or multi- or pluri-analytes).

By "several analytes", it is meant at least two analytes, even preferably 2, 3, 4 or 5 analytes.

This multi-analyte approach may be interesting for the study of autoimmune diseases ("Autoimmune disease panel"), the study of allergies ("Allergy panel"), therapy monitoring in the field of drugs, toxicology, patient's response to a treatment or inflammatory markers, for diagnostic tests of multiple infections (for example human immunodeficiency virus or HIV/hepatitis C/hepatitis B).

For example, the device according to the invention may be adapted for the determination of various antibodies in one liquid sample, namely for example anti-HIV (human immunodeficiency virus or HIV), anti-HCV (hepatitis C virus), anti-HBs (chronic viral hepatitis marker), anti-TB (tuberculosis).

By "liquid sample", it is meant any sample in which the desired analyte is in solution or in suspension.

This liquid sample may be especially any biological or body fluid.

The liquid sample may also have been obtained directly or indirectly from biological or body fluid.

The sample can also be a liquid extract of a solid sample.

Typically, the liquid sample is urine, whole blood, plasma or serum.

In some processes according to the present invention, a diluent is used when the liquid sample is plasma, serum or whole blood for example.

The diluent is deposited on the porous solid support together with the sample. Alternatively, the diluent is deposited on the porous solid support before or after the sample.

This diluent migrates in the solid support, leading to or facilitating the migration of the sample in the porous support, with the labeled detection reagent.

Typically, this diluent consists of a buffered salt solution, and may also comprise a detergent or any other component required for the reaction.

The device according to the invention is interesting in that it may be adapted for both the determination of the presence of at least one analyte, and the determination of its amount.

By "to detect" or "to determine", it is thus meant the qualitative determination (advantageously the presence or the absence) of one or more analytes in a liquid sample.

By "to detect" or "to determine", it is also meant the measurement and the quantification of one or more analytes in a sample.

Indeed, the performance of the devices and processes according to the invention also allow of embodiments for carrying out quantitative or semiquantitative measurements of one analyte or at least two different analytes in a liquid sample.

Capillary Diffusion Means

According to the present invention, by "capillary diffusion means 2", it is meant any means constituting or acting as a continuous capillary diffusion unit, through lateral migration (i.e. perpendicularly to the thickness of the capillary material(s) implemented for the capillary diffusion).

This capillary diffusion means consists advantageously in a porous solid support allowing a liquid to migrate by simple capillary diffusion.

The porosity of this support enables the capillary diffusion (or lateral migration) of the sample and/or the reagents in a liquid or wet state.

Such capillary diffusion means are very widely used in all of the immunochromatography techniques, especially lateral migration immunochromatography techniques.

Such a capillary diffusion means is for example a support elongated in the direction and/or the sense of the capillary diffusion (lateral migration).

This capillary diffusion means is comprised of:
- a single capillary or porous material, or
- many different capillary or porous elements or materials, conveniently arranged from each other (for example by overlapping), to obtain a continuous capillary flowing from an element or material to another, in the capillary diffusion direction.

Such a capillary diffusion means determines a capillary diffusion direction and sense of any liquid which is received or deposited at an upstream end, and which then moves towards a downstream end of said means.

The capillary diffusion considered according to the present invention, also called "lateral migration immunochromatographic", is to be distinguished from that is implemented in immunofiltration techniques, whereby liquids pass through the thickness of the porous filtration material(s).

As an example, these capillary diffusion means may be comprised of various immunochromatographic supports, for example, cellulose, nylon, nitrocellulose, polyethylene or glass fiber.

The capillary diffusion means may be comprised of one or more separate parts. The different parts of the support may be comprised of different materials. When the capillary diffusion means is comprised of different parts or different materials, these elements are disposed in such a way as to allow a continuous capillary flowing in the capillary diffusion means.

Typically, the capillary diffusion means is comprised of porous solid support elongated in the capillary diffusion direction. Preferably, the capillary diffusion means of the devices according to the invention comprises a porous solid support in an immunochomatographic strip form.

The capillary diffusion means is for example in the form of an immunochomatographic strip consisting of several strips superimposed or overlapping.

The device according to the invention may for example be comprised of a chomatographic strip bound to a rigid support.

The rigid support may be made of various materials such as cardboard, plasticized cardboard or more preferably, plastic materials. Preferably, the rigid support is made of polystyrene.

Advantageously, the capillary diffusion means may be included in a gripping support. This gripping support makes the capillary diffusion means handling easier and can also protect the same from moisture.

The gripping support may partially or fully wrap the capillary diffusion means.

The gripping support may be made of various materials such as cardboard, plasticized cardboard or more preferably, plastic materials. Advantageously, the gripping support is made of rigid and waterproof material.

These gripping supports or housings are especially described in the patents WO-2007/023372, EP-0 291 194, EP-0 560 411, EP-0 560 410 and EP-1 091 808.

Usually, the gripping support is in the form of a housing.

This gripping support is advantageously provided with at least one observation window to view the capture zones.

These observation windows are advantageously arranged so as to provide direct visual access only to the capture zones to be analyzed for the determination of one analyte or where appropriate, for the determination of at least two analytes.

Deposit Zone

The deposit zone 3 corresponds to a zone upstream of the capillary diffusion means 2 on which the liquid sample is provided.

This deposit zone can cooperate with a catchment system made of an absorbent material.

This catchment system can be directly contacted with for example an urine flow.

As described in WO-00/00288, the catchment system can be movable between two positions, one for collecting the liquid sample, away from the capillary diffusion means, and the other in continuity or in capillary contact with the deposit zone of the capillary diffusion means.

In an embodiment of the invention, the capillary diffusion means may comprise a zone for depositing or collecting the sample, protruding from the gripping support, to receipt the liquid sample.

In another embodiment of the invention, the gripping support or the housing has at least one opening for depositing the liquid sample.

Detection Reagent and Capture Reagent

The capillary diffusion means 2 includes over its length, on one hand, at least one detection reagent which is distributed in order to materialize the release zones 4, 6 and, on the other hand, at least one capture reagent distributed in order to materialize the capture zones 5.

By "release zone" or "capture zone" described in more details below, it is meant a localized and delimited part of the capillary diffusion means 2 on which an amount of at least one detection reagent or at least one capture reagent is deposited, respectively.

Each of the release zones 4, 6 and capture zones 5 consists advantageously in a transverse line or band (extending perpendicularly to the migration direction), having for example a width ranging from 1 to 2 mm, and a surface area ranging from 3 to 5 $mm^2$.

Generally, the "detection reagent" or the "capture reagent" consists in any chemical, biochemical or biological entity which is able to bind specifically in order to form a complex allowing the determination of said analyte in the liquid sample.

The detection reagent and/or the capture reagent are still further reagents called "binding reagents".

Such binding reagents, which allow the determination of one or more analytes in the liquid sample, are well known and can be selected for the implementation of the invention.

These binding reagents are advantageously selected from those which are able to specifically bind to said analyte and/or to each other.

According to the implemented test format, complementary binding reagents are intended to form different complexes:
    the binding reagents are able to bind concurrently to the analyte in order to form a sandwich-format test,
    one of the binding reagents (detection or capture) is able to bind to the analyte as well as to the other binding reagent (capture or detection respectively), to form a competition-format test.

In this context, at least one of the binding reagents is advantageously selected from chemical, biochemical or biological entities which are able to bind specifically to the analyte and/or to an analyte analog.

By "to bind" or "binding", it is meant any strong binding, for example covalent, as well as any weak binding, for example, of antigen/antibody or analyte/anti-analyte type.

By "anti-analyte", it is meant any chemical, biochemical or biological entity capable of specifically binding to the analyte or to the capture reagent in competition with the analyte, for example, antibody, antigen or nucleic acid.

By "suitable analyte analog", it is meant advantageously any chemical, biochemical or biological entity which is able to bind specifically to the capture reagent or detection reagent, as appropriate, in competition with the analyte.

The binding reagents are advantageously selected from antibodies, antigens or nucleic acids.

The analyte and the binding reagent form thus typically a couple able to bind specifically to each other, as for example, ligand/anti-ligand couple, antigen/antibody couple, DNA/RNA couple or DNA/DNA couple.

Thus, if the analyte is an antigen or a hapten, at least one of the binding reagents (detection reagent and/or capture reagent) is advantageously an analyte-specific antibody.

By "analyte-specific antibody", it is meant an antibody capable of specifically binding to the analyte in an antigen/antibody-type binding.

It is typically a polyclonal or monoclonal antibody having a high affinity for the analyte. Preferably, it is a monoclonal antibody.

If the analyte is an antibody, at least one of the binding reagents is advantageously the antigen recognized by the antibody.

If the analyte is a nucleic acid, at least one of the binding reagents is advantageously a complementary DNA probe.

The detection reagent(s) are advantageously conjugated to a visible and/or measurable marker, advantageously a particle marker.

By "visible and/or measurable marker", it is meant any marker allowing for direct or indirect detection with the naked eye or using an apparatus due to the signal emission at the capture zones.

The signal is for example fluorescence, coloration, presence of isotope or magnetic signal.

Examples include fluorescent or colored particle markers such as colloidal gold, colored latex particles, fluorescent latex particles and avidin and streptavidin-conjugated particles.

The colored or fluorescent particle markers consist thus in small size particles insoluble in water and which form therefore suspensions, dispersions or solutions, in liquid phase.

Markers allowing a direct observation with the naked eye include also dextran-type markers (Hansen T. M., IVD Technology 4, 35-40, 2003). The binding reagent is then conjugated to a dextran chain (derived from polysaccharide) containing fluorophores.

Markers can also consist in enzymes (including alkaline phosphatase or AP, horseradish peroxydase or HRP), colorants (or dyes) or chemiluminescent compounds (including fluorescein isothiocyanate or FITC).

In order to increase the sensitivity, an antibody labeled by techniques known to the person skilled in the art, for example, for an indirect detection, such as for example a biotinylated antibody, can be used, enabling indirectly a detection by forming avidin-biotin and streptavidin-biotin entities.

This labeled and biotinylated antibody can also be either directly yet deposited on a test line in the capture zone to increase the sensitivity, or deposited with the specific detection antibody to increase the contact time and further especially the sensitivity, for example due to the binding site number.

For its part, the analyte-specific capture reagent is immobilized on the solid support by techniques known to those skilled in the art.

This capture reagent is immobilized in such a way that it is not movable in a wet state.

This immobilization can be carried out for example by absorption or covalent coupling.

Composition of the Successive Zone Groups

The capillary diffusion means 2 thus includes one or more capture zones 5 which are complementary to a release zone 4, 6 located directly upstream (taking into account the capillary migration sense).

By "directly upstream", it is meant in particular the first release zone 4, 6 upstream of the capture zone 5.

By "complementary", it is meant the release and capture zones which constitute a zone group, the constituent binding reagents of which are selected so as to allow the implementation of a test for determining the analyte of interest, advantageously a competition format test and/or sandwich format test.

Each group of zones thus comprises a release zone followed by at least a complementary capture zone (where appropriate before the release zone of a new group of zones).

As previously discussed, this arrangement has particularly the interest of allowing the detection reagent of a release zone to be adapted in amount and/or specificity to the nearest degree and as accurately as possible according to the capture reagent constituting the capture zone(s) directly downstream.

Generally, the capillary diffusion means 2 can include:
exclusively zone groups the constituent binding reagents of which are selected so as to allow the implementation of competition-format test; or
exclusively zone groups the constituent binding reagents of which are selected so as to allow the implementation of sandwich-format test; or
at least one zone group the constituent binding reagents of which are selected so as to allow the implementation of competition-format test, and at least one zone group the constituent binding reagents of which are selected so as to allow the implementation of sandwich-format test; or
at least one zone group the constituent binding reagents of which are selected so as to allow the implementation of competition-format and sandwich-format tests, and at least one zone group the constituent binding reagents of which are selected so as to allow the implementation of competition-format and/or sandwich-format tests.

In each group of zones, the release zone and the capture zone, or the first capture zone of a series, can be confused.

Alternatively, the capture zone, or the first capture zone of a series, is separated from the release zone by advantageously a distance of few millimeters, for example ranging from 2 to 4 mm.

The capture zones of a series are in addition separated from each other by advantageously a distance of few millimeters, for example ranging from 1 to 4 mm.

Even generally, the upstream release zone can be located in the sample depositing or receiving zone.

But, this upstream release zone can also be deposited in a dry state, downstream of the sample depositing or receiving zone to prevent any detection reagent loss by a washing effect when depositing the sample.

Even generally, the number of capture zones materialized on the capillary diffusion means, complementary to a release zone located directly upstream, is advantageously from 1 to 10, preferably from 2 to 5 (that is still a number selected from 1, 2, 3, 4, 5, 6, 7, 8, 9, 10).

Such an approach is particularly useful to obtain semi-quantitative or quantitative type results.

Indeed, as illustrated in the Examples, the signal profile obtained on the successive capture zones can be attributed to an analyte concentration range in the liquid sample. As illustrated in the Examples, the signal profile obtained on the successive capture zones can also be attributed to a precise analyte concentration value in the liquid sample.

Also, the Example part further shows that, surprisingly, the hook effect can be significantly reduced using a particular arrangement of release and capture zones for implementing a sandwich test.

In this regard, it is shown that an interesting embodiment comprises:
an upstream zone group comprising the release zone/capture zone couple or two capture zones, and then
a downstream zone group comprising at least a new release zone followed by a series of capture zones.

This upstream zone group is advantageously based on a sandwich format so as to ensure the upstream capture of analyte(s):

either a significant portion of analyte(s), or a portion corresponding to a detection threshold with a diagnostic value (the "diagnostic value" refers to any analyte (or biomarker) concentration scientifically recognized as threshold allowing medical interpretation).

In particular, this scheduled upstream capture allows the concentration to be controlled in the liquid sample wending his way through the subsequent zone group(s).

The presence of this upstream zone group would present the interest of controlling the hook effect in the downstream zone group(s).

Still generally, the concentration of detection reagent within the release zone and that of the capture reagent within the complementary capture zones is advantageously adjusted for, in particular, the desired diagnostic value concentration ranges, according to the concentration nomenclature expressed in ng/mL or in international unit (IU)/mL This concentration is for example between 0.1 and 1 ng/linear cm of the porous support, depending on the binding reagent specificities.

Furthermore, the number of release zones, and therefore, that of the corresponding zone groups, is from 1 to 4 (that is still a number selected from 1, 2, 3 or 4). The preferred range would be for example two groups for a capillary support length of 25 mm.

The selection of the binding reagents for the related zones is made conventionally per se.

In a competition test, the release zones 4, 6 and complementary capture zones 5 comprise advantageously:

(i) a detection reagent labeled as the analyte itself, or a suitable analyte analogue, conjugated to a visible and/or measurable marker, and (ii) an immobilized capture reagent, advantageously an antibody type anti-analyte, capable of specifically binding to the analyte in the sample and to the aforementioned detection reagent.

This embodiment enables the detection of the liquid sample analyte by a test in which a competition occurs at the complementary capture zone(s) between, on one hand, the sample analyte and, on the other hand, the labeled analyte or the labeled analyte analog.

Alternatively, still in a competition test, the release zones 4, 6 and complementary capture zones 5 comprise advantageously:

(i) a detection reagent labeled as an anti-analyte, for example, an analyte- or analyte analogue-specific antibody, conjugated to a visible and/or measurable marker, and (ii) a capture reagent as the analyte itself, or an analyte analogue, immobilized in at least one of the capture zones 5 of the capillary diffusion means 2.

This embodiment enables the detection of the liquid sample analyte by a competition test in which the detection reagent is capable of binding, in competition, to either the sample analyte or the capture reagent.

In these different competition tests, the immobilized complex labeled detection reagent/capture reagent forms in the absence of the analyte of interest in the sample. These immobilized complexes thus generate a visible and/or measurable signal such as defined above, in the absence of analyte.

In the presence of analyte, there is no immobilization of the labeled detection reagent at the capture reagent. The absence of signal at the capture zone thus corresponds to the presence of the analyte in the sample.

In a sandwich-type test, the release zones 4, 6 and the complementary capture zones 5 comprise advantageously:

(i) a detection reagent labeled as an anti-analyte conjugated to a visible and/or measurable marker, which binds specifically to the analyte, and (ii) an immobilized capture reagent specifically binding to the analyte, also advantageously an anti-analyte.

According to a preferred embodiment of this sandwich format embodiment, at least one of the release zones 4, 6 of a zone group 7 comprises one or more antibodies specific to the analyte or to at least one analyte, conjugated to a visible and/or measurable marker, which are deposited in a dry state in or on the capillary diffusion means, but which are free to migrate by capillary diffusion in a wet state.

In this case, the complementary capture zone(s) 5 of this zone group 7 comprise one or more analyte-specific antibodies which are immobilized by known techniques. These antibodies are immobilized in such a way that they are not movable in a wet state.

Antibodies of a release zone 4, 6 and of the complementary capture zone(s) 5 bind respectively and specifically to the analyte, for example, on two epitopic sites, identical or different from the analyte.

The complexes analyte/antibody obtained are immobilized at the capture zone(s) 5 of the zone group 7. These immobilized complexes thus generate a visible and/or measurable signal such as defined above.

For detecting a single analyte, the detection reagent(s) of the release zones and/or the capture reagent(s) of the capture zones are advantageously capable of specifically binding to said analyte.

The successive zone groups are thus advantageously dedicated to a single analyte.

In this case, the release zones include advantageously one or more detection reagents identical to each other, and the capture zones include one or more capture reagents identical to each other.

All of the different successive zone groups are thus adapted for the implementation of a test of the same format, that is to say competition or sandwich.

Alternatively, the release zones include each advantageously a specific detection reagent, and the complementary capture zones include a complementary capture reagent.

In this case, the different successive zone groups can be adapted for the implementation of tests identical or different from each other, that is to say competition or sandwich.

For the detection of at least two analytes, the detection reagents of a release zone and/or the capture reagent of the complementary capture zone(s), immediately downstream of said release zone and forming together a zone group, are advantageously capable of specifically binding to one of said analytes to be determined.

In this case, each zone group is advantageously dedicated to one of the analytes.

The different successive zone groups can be adapted for the implementation of tests identical (competition or sandwich) or different from each other (competition and sandwich).

According to an interesting embodiment, each zone group comprises a final capture zone downstream to the capture zones of said zone group.

This final capture zone comprises an immobilized reagent which is capable of specifically binding to the labeled detection reagent derived from the release zone of said zone group.

This embodiment can be used as a control zone; it has also the interest of allowing a capture of the labeled detection reagent at the end of this zone group in such a way that it does not attain a zone group located downstream and in order to prevent any interference phenomenon.

Even generally, the release zones 4, 6 and complementary capture zones 5 of a zone group 7 comprise advantageously:

(i) a detection reagent labeled as an anti-analyte, for example an analyte- or analyte analogue-specific antibody, conjugated to a visible and/or measurable marker, (ii) a capture reagent as the analyte itself, or an analyte analogue, immobilized in at least one of the capture zones 5 of the capillary diffusion means 2, and (iii) an immobilized capture reagent specifically binding to the analyte, also advantageously an anti-analyte, immobilized in another of the capture zones 5 of the capillary diffusion means 2.

The latter embodiment allows the simultaneous implementation of a sandwich-format test and a competition-format test, within a single zone group 7.

Particular Embodiments

A first embodiment in accordance with the invention is shown on the FIG. 1.

This device is adapted for the qualitative determination of an analyte of interest likely to be present in the liquid sample.

The capillary diffusion means 2 include two zone groups 7:
an upstream group 71 consisting of the upstream release zone 4 and an upstream capture zone 51, complementary to each other, and
a downstream group 72 consisting of the downstream release zone 6 and a downstream capture zone 52, complementary to each other.

In each zone group 7, the respective binding reagents are selected for implementing a detection of the analyte of interest by a competition test or a sandwich test as described above.

These two zone groups 7 are thus adapted for implementing:
a single competition test or a single sandwich test,
a competition test for one group and a sandwich test for the other group.

In any case, the presence of a release zone 4, 6 upstream of each capture zone 5 enables a tight adaptation of the concentration in the couple release zone/capture zone.

The determination of a single analyte can be yet implemented by means of various devices in accordance with the invention, with their specific benefits.

Figure 2:
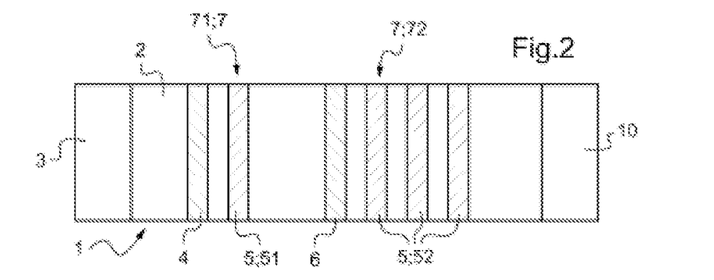
FIG. 2 depicts, even schematically, a second device according to the invention for the determination of a single analyte, comprising a first zone group consisting of a release zone and a capture zone, and then a second zone group consisting of a release zone followed by several capture zones.
Figure 3:
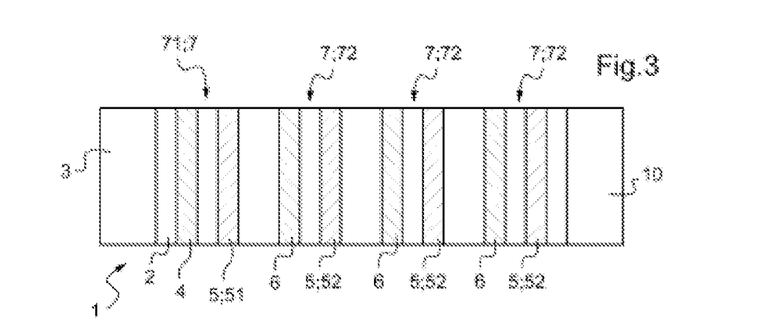
FIG. 3 illustrates, also schematically, a third device according to the invention for the determination of a single analyte, comprising several zone groups each consisting of a release zone and a capture zone.

FIGS. 2 and 3 show such other devices, the capillary diffusion means 2 of which includes an upstream zone group 71 comprising:
the upstream release zone 4, and
a first capture zone 51, complementary to said upstream release zone 4.

As appropriate, two variations are feasible for the zone group(s) 72 directly downstream.

In a first variation according to FIG. 2, the capillary diffusion means 2 still includes a downstream zone group 72 comprising:
a downstream release zone 6, and then
several successive second capture zones 52, here three, complementary to said downstream release zone 6.

This embodiment has the interest of providing a particularly reliable semi-quantitative result, avoiding the hook effect.

According to this embodiment, for determining hCG hormone, an upstream zone group 71, the reagent concentration and specificity of which are adjusted, can be envisioned to detect only the hCG hormone concentration corresponding to the first day of missed period, i.e. of about 20 mIU/mL The downstream release zone 6 contains a detection reagent the concentration of which is higher than that is present at the upstream release zone 4, allowing the detection and the distinction of various analyte concentrations at the second downstream successive capture zones 52.

In this format, for hCG hormone concentration corresponding to the first day of missed period, a visual and measurable detection signal only at the first capture zone 51 has been thus found.

For hCG hormone concentration corresponding to one or more weeks of pregnancy, the visual and measurable signal will successively occurs at the second capture zones 52 downstream of the downstream release zone 6, providing a hCG hormone concentration semi-quantitative analysis of the tested sample.

According to the same implementation format, from reagents suitable for determining prostate-specific antigen (or PSA), the "diagnostic value threshold concentration" (4 ng/mL) can be detected and distinguished from other higher concentrations of the same analyte (up to 200 ng/mL), allowing again a semi-quantitative approach.

Again, according to the same format, by means of reagents suitable for the determination of blood (hemoglobin) in the stool (FOB or Fecal Occult Blood test), the "diagnostic value threshold concentration" (40 ng/mL) can be detected and distinguished from higher concentrations of the same analyte (up to 1000 ng/mL and more), providing thus a semi-quantitative result.

According to an unrepresented alternative of the first variation according to FIG. 2, the upstream zone group 71 comprises a second capture zone, also complementary to the upstream release zone 4.

This second capture zone is located downstream of the upstream release zone 4 and the first capture zone 51, but yet upstream of the downstream zone group 72.

In this instance, the capillary diffusion means 2 includes a first zone group 7 upstream, comprising:
the upstream release zone 4,
two successive upstream capture zones 51, complementary to said upstream release zone 4,
and then a second zone group 7, downstream, comprising:
the downstream release zone 6, and
several second successive capture zones 52, here three, complementary to said downstream release zone 6.

In a second variation according to FIG. 3, the diffusion means 2 further includes successive downstream zone groups 72, here three, each comprising:
a release zone 6, and
a capture zone 52, complementary to said related release zone 6.

In the case of determining a single analyte, this embodiment has the interest of optimizing the detection threshold in the successive release and capture zones.

In this variation, it may be interesting to increase gradually the detection reagent concentration within the successive release zones 4, 6 from upstream to downstream, while retaining an identical capture reagent concentration in each of the capture zones 52.

This approach has an interest in the context of an analyte detection having a diagnostic value at various concentration values (threshold) (for example hCG, PSA or hemoglobin).

According to another approach of the invention, the release zones and capture zones can be tailored for the determination of several analytes.

Figure 4:
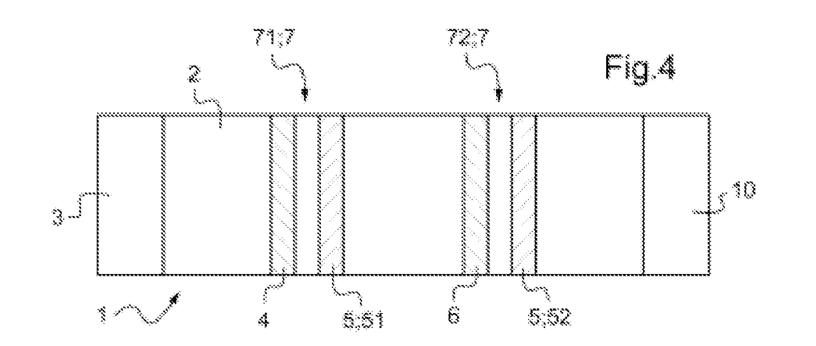
FIG. 4 shows, even schematically, a fourth device according to the invention for the determination of two analytes, comprising two zone groups each consisting of a release zone and a capture zone, each dedicated to one of said analytes.

In this regard, according to an embodiment depicted on FIG. 4, the capillary diffusion means 2 includes many successive zone groups 7, in this instance two, each consisting of a release zone 4, 6 and a complementary capture zone 5.

In this instance, the upstream zone group 71 is adapted for the determination of a first analyte by a suitable test (competition or sandwich); the downstream zone group 72 is adapted for the determination of a second analyte by a suitable test (competition or sandwich).

Such a device would further include one or more other additional zone groups 7, each adapted for one analyte to be determined.

Figure 5:
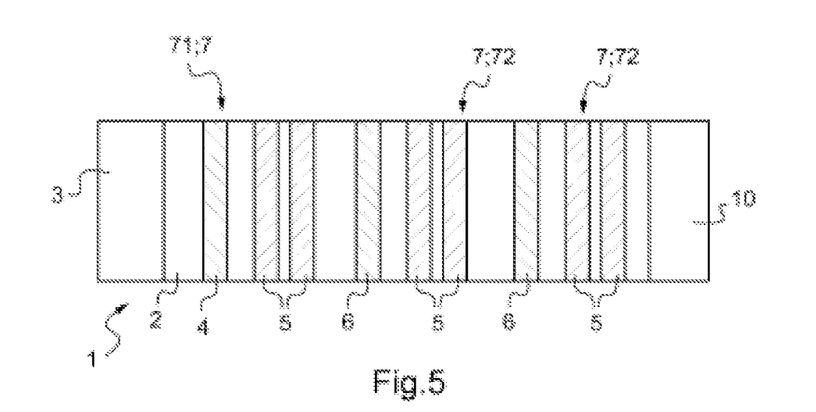
FIG. 5 depicts, still schematically, a fifth device according to the invention for the determination of several analytes, comprising several zone groups each consisting of a release zone and two capture zones, each dedicated to one of the analytes.

Alternatively, according to an embodiment depicted on FIG. 5, the capillary diffusion means 2 includes zone groups 7, here three, each consisting of a release zone 4, 6, followed by several complementary capture zones 5 (here two).

Again, each zone group 7 is adapted for the determination of one of the analytes by a suitable test (competition and/or sandwich).

The presence of several capture zones 5 within each zone group 7 make it possible to obtain a semi-quantitative value for each of these analytes.

These different embodiments are not limitative in any way. The various zone groups 7 and their respective compositions can be adapted in any way.

Control Zone

In a preferred embodiment of the invention and as depicted on FIGS. 1 to 5, the device 1 further includes a control zone 10 which is formed downstream and which comprises a control capture reagent.

This control zone 10 enables to have a positive control in order to ensure the effective capillary diffusion of the liquid sample from the depositing zone 3 to the capture zones 5 of the capillary diffusion means 2.

This control zone 10 is consisting of a capture reagent which is immobilized permanently downstream of the capillary diffusion means 2.

It can be, for example, an antibody binding to the detection reagent(s) constituting the release zones 4, 6. In this case, this control capture reagent allows the migration of the detection reagent(s) through the capture zones 5 to be checked.

Alternatively, this control capture reagent is independent from the analyte and simply allows the liquid sample diffusion along the capillary diffusion medium 2 to be checked.

Implementation

Such a device can be implemented according to the method or instructions for use defined hereinafter:

a) the liquid sample is deposited in the depositing zone 3 of the capillary diffusion means 2, b) a period of time sufficient for the capillary diffusion migration of the liquid sample to the capture zones 5, where appropriate to the control zone 10, is allowed to elapse, c) the extent to which, at the capture zones 5:

c.1) the detection reagent, complexed with the analyte, binds to the complementary capture reagent of its zone group 7 (sandwich format), and/or c.2) the detection reagent binds to the capture reagent of its zone group 7 (competition format), is observed, then d) the analyte(s) are qualitatively and/or semi-quantitatively and/or quantitatively determined from the obtained results.

In practice, during the capillary migration according to step c), the liquid sample passes successively through each of the serially formed zone groups 7.

In each zone group 7 implementing a sandwich-format test, any analytes present form a complex with the detection reagents from its release zone 4 or 6.

The complexes thus formed progress to the complementary capture zone 5 where they are immobilized by the corresponding capture reagents.

The complexes thus retained provide visible and/or measurable signal at this capture zone, allowing the presence of the analyte of interest to be determined in said liquid sample.

As appropriate, the signal strength increases at the successive capture zones, distributed over the zone group(s) until gradual depletion of the labeled complexes.

The signal strength is advantageously measured by means of a suitable optical scanner. This signal strength is for example expressed in pixel number, detected on all or part of the capture zone 5.

In this context, the device of the invention is particularly interesting when it includes several successive capture zones for a single analyte, to overcome the hook effect and to obtain a semi-quantitative result.

In this regard, the signal strength at each capture zone is compared to that of the other successive capture zones.

Part of the complexes formed between the detection reagents of the release zone and the analyte is captured by each successive capture zone, until gradual depletion of the analyte in the migrating liquid sample.

The signal strength at each capture zone thus increases relative to the preceding capture zone, up to a capture zone where this strength is at its maximum. This capture zone is then followed by capture zones where the signal strength decreases.

Standard solutions are previously implemented on an identical device so as to be able to assign a result profile with an analyte semi-quantitative result in the liquid sample.

It is then possible to change this result into a semi-quantitative value by pre-assigning each capture zone to an analyte concentration range in the liquid sample.

In a zone group 7 implementing a competition-format test, any analytes present prevent the formation of complexes between the detection reagent from its release zone 4 or 6 and the capture reagent of the complementary capture zone(s) 5.

In the absence of analyte, the complexes are formed and create a visible and/or measurable signal at the corresponding capture zone.

Again, the device of the invention is particularly interesting when it includes several successive capture zones for a single analyte, to overcome the hook effect and to obtain a semi-quantitative result.

The results can be interpreted semi-quantitatively in relation to the analyte concentration, such as for example, low, medium, high and very high.

Standard solutions are previously implemented on an identical device so as to assign here again a result profile with an analyte semi-quantitative result in the liquid sample.

It is then possible to change this result into a semi-quantitative value by pre-assigning each capture zone to an analyte concentration range in the sample. Generally, the determination device can also allow the quantitative determination of an analyte.

The visual result obtained can thus be changed for example into a concentration expressed for example in ng/mL or mIU/mL of the analyte in the liquid sample to be assayed.

For that purpose, standard solutions are implemented on the determination device so as to be able to assign a strength profile with an analyte quantitative value in the liquid sample.

For example, the signal strength (pixel number) is measured at each capture zone.

For each zone group, the signal strengths measured on these capture zones are subsequently added up.

The strengths that were respectively added of the different zone groups are changed into a ratio corresponding to the added strengths of a zone group relative to the added strengths of another zone group.

If required, these ratios are then subjected to an interpolation, for example a linear interpolation, advantageously associated with a proportional coefficient for each predetermined range of the analyte concentration, to obtain a standard curve corresponding to the strength ratio (in abscissa) as a function of the analyte concentration in the liquid sample (in ordinate).

It is then possible to associate a strength ratio obtained for an analyzed sample with a quantitative value of the analyte in said liquid sample, taking into account the aforementioned standard curve.

In a particular embodiment, the detection and capture reagents are applied on the support so as to obtain:
- an upstream zone group comprising two capture zones T1 and T2, after a $1^{rst}$ release zone L1, and
- an downstream zone group comprising three capture zones T3, T4 and T5, after a $2^{nd}$ release zone L2.

In this instance, the cumulative strength ratio is assessed advantageously by the following formula (I):

Cumulative strength ratio=(Sum of the strength of the three downstream capture zones $T3,T4$ and $T5$)/ (Sum of the strength of the two upstream capture zones $T1$ and $T2$)

The cumulative strength ratio enables the construction of a signal curve (strength) as a function of the analyte concentration in the liquid sample to be analyzed.

Such a quantitative analysis is further illustrated in Example 2 below.

EXAMPLE

Example 1

Lateral Flow Immunochromatographic Device for the Determination of an Analyte Having a Hook Effect Hook effect evaluation was carried out through determination tests of hCG semi-quantitative concentration values by lateral flow immunochromatography.

For the record, in order to counteract the hook effect, the determination devices are usually provided with an excess of labeled antibodies at the single release zone.

By excess of antibody, it is meant an antibody concentration significantly higher than the concentration required for determining the diagnostic interest threshold.

Various devices were constructed from "hCG matched pairs antibodies" offered for example by the Fitzerald Company (mono/polyclonal antibody).

Anti-hCG antibodies were labeled with colloidal gold (Aldrich Sigma) according to the standard methodology (for example the technique developed by the Organon Teknika Company).

Anti-hCG antibodies were printed on the nitrocellulose membrane (NC) of the Millipore Company according to different arrangements described in detail hereafter (Tests 1 to 5).

The concentration of these deposited antibodies is adjusted so as to obtain a concentration of from 0.5 to 1 µg/mL The pads (or strips) of 4 mm were tested with different concentrations of hCG hormones (Sigma) diluted in hCG-negative urine. The dilutions tested are 0, 25, 50, 100, 1 000, 5 000, 50 000, 100 000, 250 000 and 500 000 mIU/mL These different concentrations correspond each to a stage of the pregnancy in normal conditions (respectively 0, 1, 2, 3, 4, 5, 6, 9 to 12, 13 to 16 weeks of pregnancy).

The test protocol consists in applying 150 µL of each dilution on the pad deposit zone; after 3 to 5 minutes, the presence of the coloration strength is observed on the capture zone(s) of each pad.

The results are recorded and interpreted following the criteria generally adapted for the reading of qualitative tests of this type, namely:
- 0: absence of coloration
- ±: slight coloration, doubtful, border-line, ghost-line, not easily visible
- +: pale coloration but clearly visible
- ++: clearly visible line
- +++: intense line coloration
- ++++: very intense line coloration Test 1: Device with a Single Release Zone and a Single Capture Zone (Test Line 1)

The results obtained are shown in Table n°1 below.

TABLE 1

| Week of pregnancy | Concentration hCG mIU/ml | Ø | ± | + | ++ | +++ | ++++ |
|---|---|---|---|---|---|---|---|
| 0 | 0 | X | | | | | |
| 1 | 25 | | X | | | | |
| 2 | 50 | | | X | | | |
| 3 | 100 | | | | X | | |
| 4 | 1000 | | | | | | X |
| 5 | 5000 | | | | | | X |
| 6 | 50000 | | | | | X | |
| 9-12 | 100000 | | | | X | | |
| 13-16 | 250000 | | X | | | | |
| | 500000 | | X | | | | |

The rapid test by lateral flow immunochromatography shows a linearity of the dose/response curve between 1000 and 5000 mIU/ml of hCG.

From this maximum concentration, the signal strength loss is emerging because of the hook effect ("high dose hook effect").

As a result, a test of this type can not differentiate, in certain coloration strengths of the result, if the hCG concentration is of 50 mIU/mL or 100 000 mIU/mL Test 2: Device with a Single Release Zone and Two Successive Capture Zones (Test Line 1 and Test Line 2)

Pads containing a second capture line (test line 2) were produced and then tested with the same hCG concentration panel.

The results obtained are shown in Table n°2 below.

TABLE 2

| Concentration hCG mIU/ml | Coloration strength | | | | | | | | | | | |
|---|---|---|---|---|---|---|---|---|---|---|---|---|
| | Test line 1 | | | | | | Test line 2 | | | | | |
| | Ø | ± | + | ++ | +++ | ++++ | Ø | ± | + | ++ | +++ | ++++ |
| 0 | X | | | | | | X | | | | | |
| 25 | | X | | | | | X | | | | | |
| 50 | | | X | | | | | X | | | | |
| 100 | | | | X | | | | | X | | | |
| 1000 | | | | | X | | | | | X | | |
| 5000 | | | | | X | | | | | | X | |
| 50000 | | | X | | | | | | | | | X |

TABLE 2-continued

| Concentration | Coloration strength | | | | | | | | | | | |
|---|---|---|---|---|---|---|---|---|---|---|---|---|
| | Test line 1 | | | | | | Test line 2 | | | | | |
| hCG mIU/ml | Ø | ± | + | ++ | +++ | ++++ | Ø | ± | + | ++ | +++ | ++++ |
| 100000 | | X | | | | | | X | | | | |
| 250000 | X | | | | | | X | | | | | |
| 500000 | X | | | | | | X | | | | | |

The hook effect is reported to a higher concentration. Indeed, it appears that introducing a second capture line shifts the concentration threshold of the hook effect to a higher concentration zone.

Test 3: Device with a Single Release Zone and Three Successive Capture Zones (Test Line 1, Test Line 2 and Test Line 3)

Pads containing a third capture line (test line 3) were produced and then tested with the same hCG concentration panel.

The results obtained are shown in Table n°3 below.

TABLE 3

| Pregnancy week | Concentration hCG mIU/ml | Coloration strength | | | | | | | | | | | | | | | | | | |
|---|---|---|---|---|---|---|---|---|---|---|---|---|---|---|---|---|---|---|---|---|
| | | Test line 1 | | | | | | Test line 2 | | | | | | Test line 3 | | | | | | |
| | | Ø | ± | + | ++ | +++ | ++++ | Ø | ± | + | ++ | +++ | ++++ | Ø | ± | + | ++ | +++ | ++++ |
| 0 | 0 | X | | | | | | X | | | | | | X | | | | | |
| 1 | 25 | | X | | | | | X | | | | | | X | | | | | |
| 2 | 50 | | | X | | | | | X | | | | | X | | | | | |
| 3 | 100 | | | | X | | | | | X | | | | | X | | | | |
| 4 | 1000 | | | | | X | | | | | X | | | | | X | | | |
| 5 | 5000 | | | | | X | | | | | | X | | | | | X | | |
| 6 | 50000 | | | | X | | | | | | | X | | | | | X | | |
| 9-12 | 100000 | | | X | | | | | | | X | | | | | X | | | |
| 13-16 | 250000 | | X | | | | | | X | | | | | | X | | | | |
| | 500000 | X | | | | | | X | | | | | | X | | | | | |

The third capture line (test line 3) does not shift anymore the hook effect. This is likely due to a depletion of the labeled antibodies of the release zone.

Test 4: Device with a Single Release Zone and Three Successive Capture Zones

According to the conclusion of the test n°3, we maintained the three capture zones while doubling the labeled antibody concentration of the single release zone.

It was found that this configuration is prone to strong background, making the test unreadable and unusable.

Test 5: Device with Two Release Zones and Four Capture Zones

A second release zone was introduced after the first capture line (test line 1), succeeded by 3 complementary lines of capture antibodies. This configuration corresponds to the embodiment such as described above in relation with FIG. 2.

This new platform was tested with the same hCG concentration panel. The results obtained are summarized in Table n°4 below.

Introducing a second release zone complemented with 3 successive capture lines allows asserting in which concentration range does the signal obtained lie in the first capture line (test line 1) and, therefore, pronouncing on the concentration range, referring semi-quantitatively to the stage of the pregnancy.

This approach provides a solution to the hook effect problem.

TABLE 4

| Pregnancy week | Concentration hCG mIU/ml | Coloration strength | | | | | | | | | | | | | | | | | | | | | | | |
|---|---|---|---|---|---|---|---|---|---|---|---|---|---|---|---|---|---|---|---|---|---|---|---|---|---|
| | | TEST ZONE 1 | | | | | | TEST ZONE 2: capture lines placed after the 2nd release zone | | | | | | | | | | | | | | | | | |
| | | Test line 1 | | | | | | Test line 2 | | | | | | Test line 3 | | | | | | Test line 4 | | | | | |
| | | Ø | ± | + | ++ | +++ | ++++ | Ø | ± | + | ++ | +++ | ++++ | Ø | ± | + | ++ | +++ | ++++ | Ø | ± | + | ++ | +++ | ++++ |
| 0 | 0 | X | | | | | | X | | | | | | X | | | | | | X | | | | | |
| 1 | 25 | | X | | | | | X | | | | | | X | | | | | | X | | | | | |
| 2 | 50 | | | X | | | | | X | | | | | X | | | | | | X | | | | | |
| 3 | 100 | | | | X | | | | | X | | | | | X | | | | | X | | | | | |
| 4 | 1000 | | | | | X | | | | | X | | | | | X | | | | | X | | | | |
| 5 | 5000 | | | | | X | | | | | | X | | | | | X | | | | | X | | | |
| 6 | 50000 | | | | X | | | | | | | X | | | | | X | | | | | X | | | |

TABLE 4-continued

| Pregnancy week | Concentration hCG mIU/ml | TEST ZONE 1 Test line 1 | | | | | | TEST ZONE 2: capture lines placed after the 2nd release zone | | | | | | | | | | | | | | | | | |
|---|---|---|---|---|---|---|---|---|---|---|---|---|---|---|---|---|---|---|---|---|---|---|---|---|---|
| | | | | | | | | Test line 2 | | | | | | Test line 3 | | | | | | Test line 4 | | | | | |
| | | Ø | ± | + | ++ | +++ | ++++ | Ø | ± | + | ++ | +++ | ++++ | Ø | ± | + | ++ | +++ | ++++ | Ø | ± | + | ++ | +++ | ++++ |
| 9-12 | 100000 | | X | | | | | | X | | | | | | X | | | | | | X | | | | |
| 13-16 | 250000 | X | | | | | | X | | | | | | X | | | | | | X | | | | | |
| | 500000 | X | | | | | | X | | | | | | X | | | | | | X | | | | | |

Example 2

Lateral Flow Immunochromatographic Device for the Quantitative Determination of an Analyte Having a Hook Effect Materials The immunochromatographic device comprises a porous support as a nitrocellulose membrane, preferably, with a pore size of between 8 and 15 micrometers and a width of between 2 and 3 cm.

The porous materials for sample pad, for conjugate pad and for absorbent pad were selected from a multiple choice of cellulose and glass fiber paper suppliers, with a thickness of between 0.2 and 1.0 mm depending on the application and a porosity of between 100 and 200 micrometers.

Antibodies were constructed from hCG matched pairs antibodies offered by the BiosPacific company (mono/polyclonal antibody).

Anti-hCG and anti Beta-hCG monoclonal and polyclonal antibodies are preferably at a concentration of 1 mg/mL in a buffered solution PBS.

Anti-hCG antibodies were labeled with colloidal gold (Aldrich Sigma) according to the standard methodology (for example the technique developed by the Organon Teknika Company).

Anti-hCG antibodies were printed on the nitrocellulose membrane (NC) of the Millipore Company.

The concentration of these deposited antibodies is adjusted so as to obtain a concentration of from 0.5 to 1 µg/mL.

The colloidal gold for the preparation of release reagents (marker) is preferably at a concentration of from 10 to 15 OD/mL, and of a particle size between 20 and 60 micrometers.

A hCG control range (Sigma) was prepared and calibrated (according to the international standard NIBSC) in order to obtain hCG concentrations ranging from 0 mIU/mL to 1 000 000 mIU/mL, required to assess the performance of the test and its quality control. The tested dilutions are 0, 25, 250, 2500, 25 000, 250 000, 500 000 and 1 000 000 mIU/mL.

Method

Detection and capture reagents are applied on the nitrocellulose support in order to obtain:
- a first release zone L1, advantageously on a conjugate pad interposed between a sample pad and a membrane printed on PVC support,
- two upstream capture zones T1 and T2, after the $1^{st}$ release zone L1,
- a $2^{nd}$ release zone L2, and
- three downstream capture zones T3, T4 and T5, after the $2^{nd}$ release zone L2.

The $2^{nd}$ release zone L2 is arranged between the second upstream capture zone T2 and the first downstream capture zone T3, in order to advantageously ensure a distance of at least two millimeters between them.

The concentrations of the release zone and the capture zone reagents are adjusted to ensure the detection of the desired hCG analyte at the given concentrations (0 to 1 000 000 mIU/mL).

After applying the reagents, the nitrocellulose support is dried in programmed temperature and humidity conditions (generally 1 h at 37° C.).

After drying, the nitrocellulose support printed with reagents is used to build a mastersheet format test ("bande de test à couper en bandelette"), comprising a PVC support, the printed nitrocellulose membrane, a conjugate pad ($1^{st}$ release zone), a sample pad and an absorbent pad.

The sample pad, the conjugate pad and the absorbent pad are porous materials arranged on the PVC support with a printed nitrocellulose membrane, adapted and optionally immuno-chemically treated so as to actually receive the sample (sample pad), to filter it, to ensure its reaction with reagents in the $1^{st}$ release zone (conjugate pad), to provide uniform migration on the membrane and eventually to absorb the excess of reagents and to stop the migration (absorbent pad).

The mastersheet is then cut to obtain pads of from 2 to 6 mm width, preferably, from 4 mm or 5 mm width.

The pads are then enclosed in a rectangular shaped plastic housing (cassette format device), ready for use.

Test Procedure

Different hCG concentrations are prepared to obtain a control range spanning the concentration range of from 0 to 1 million mIU/mL of hCG hormone.

Each concentration is tested in duplicate.

Generally, between 100 and 200 microliters of sample of each hCG concentration are applied on the different test units.

The reaction is observed for a maximum of 10 minutes.

The results obtained are assessed with the naked eye (concentration range).

Then, the results obtained are recorded by optical reading means (instrument or reader) allowing the strength of each capture line to be measured (expressed in pixels).

The quantitative result (numerical result) provided by the reader is calculated from an algorithm the basic calculation of which takes into account the cumulative strength ratio according to the following formula (I):

Cumulative Strength Ratio(CSR)=(Sum of the Strength of Three downstream capture zones T3,T4 and T5)/(Sum of the strength of two upstream capture zones T1 and T2)   Formula(I)

The results obtained in the present experimental conditions are shown in Table 5 below.

The cumulative strength ratio increases with the analyte concentration in the liquid sample.

By interpolation, cumulative strength ratio allows to construct a curve of the signal (strength) as a function of analyte concentration in the liquid sample.

It is then possible to determine the hCG concentration in a liquid sample on a range of from 0 to 1 000 000 mIU/mL, taking into account this curve of signal and cumulative strength ratio measured on said determination device in the presence of said liquid sample.

TABLE 5

| hCG analyte concentration in mIU/mL | STRENGTH IN PIXELS/CAPTURE LINE | | | | | | | |
|---|---|---|---|---|---|---|---|---|
| | 0 | 25 | 250 | 2500 | 25000 | 250000 | 500000 | 1000000 |
| Capture Line T1 | 18886 | 108928 | 234085 | 278087 | 176567 | 29346 | 16915 | 10131 |
| Capture Line T2 | 17316 | 81398 | 173706 | 246662 | 146653 | 41915 | 24346 | 10415 |
| Total 2 lines | 36202 | 190326 | 407791 | 524749 | 323220 | 71261 | 41261 | 20546 |
| Capture Line T3 | 6295 | 33339 | 113129 | 229576 | 142516 | 45046 | 28946 | 13308 |
| Capture Line T4 | 1965 | 28398 | 111021 | 164484 | 164342 | 42531 | 34208 | 15331 |
| Capture Line T5 | 3502 | 30833 | 61406 | 99659 | 121671 | 36346 | 38123 | 22162 |
| Total 3 lines | 11762 | 92570 | 285556 | 493719 | 428529 | 123923 | 101277 | 50801 |
| Total Ratio Pixel (T3 + T4 + T5)/ (T1 + T2) | 0.325 | 0.486 | 0.700 | 0.941 | 1.326 | 1.739 | 2.455 | 2.473 |

The invention claimed is:

1. Device for the determination of the presence and/or the amount of at least one analyte capable of being contained in a liquid sample, comprising a capillary diffusion means (2) on which said liquid sample is intended to migrate laterally according to a direction and a sense of capillary migration, and on which are materialized, in said upstream to downstream capillary migration sense, at least:
one zone (3) for depositing the liquid sample,
one upstream release zone (4) which comprises at least one detection reagent conjugated to a visible and/or measurable marker, said detection reagent being capable to move as a consequence of the migration of the liquid sample in said capillary diffusion means, and
at least two capture zones (5) which comprise each at least one capture reagent immobilized on said capillary diffusion means,
characterized in that said device (1) further comprises at least one downstream release zone (6) which is materialized on said capillary diffusion means (2) and which is located downstream of at least one of said capture zones (5),
which downstream release zone (6) comprises also at least one detection reagent conjugated to a visible and/or measurable marker, said detection reagent being capable to move as a consequence of the migration of the liquid sample in the capillary diffusion means (2), and
in that the detection reagent of a release zone (4, 6) and/or the capture reagent of the complementary capture zone(s) (5), located directly downstream of said release zone (4, 6), are capable of specifically binding to said analyte and/or specifically binding to each other to form a complex allowing the determination of said analyte in said liquid sample at said complementary capture zone(s) (5).

2. Device for determination according to claim 1, characterized in that the downstream release zone(s) (6) are each inserted between two capture zones (5).

3. Device for determination according to claim 2, characterized in that it comprises an upstream group of zones (71) comprising an upstream capture zone (51) located directly downstream of the upstream release zone (4), which upstream group of zone (71) being itself followed by one or more zone group(s) (72) each comprising a release zone (6) and one or more complementary capture zones (5).

4. Device for determination according to claim 1, characterized in that it comprises an upstream group of zones (71) comprising an upstream capture zone (51) located directly downstream of the upstream release zone (4), which upstream group of zone (71) being itself followed by one or more zone group(s) (72) each comprising a release zone (6) and one or more complementary capture zones (5).

5. Device for determination according to claim 1, for the determination of a single analyte, characterized in that the detection reagent(s) of the release zones (4, 6) and/or the capture reagent(s) of the capture zones (5) are capable of specifically binding to said analyte.

6. Device for determination according to claim 5, characterized in that the release zones (4, 6) include one or more detection reagents identical to each other, and in that the capture zones (5) include one or more capture reagents identical to each other.

7. Device for determination according to claim 6, characterized in that the capillary diffusion means (2) includes:
the upstream release zone (4),
one or two upstream capture zone(s) (51), complementary to said upstream release zone (4), and then
a downstream release zone (6), and
at least two second capture zones (52), complementary to said downstream release zone (6).

8. Device for determination according to claim 6, characterized in that the capillary diffusion means (2) includes:
the upstream release zone (4),
one or two upstream capture zone(s) (51), complementary to said upstream release zone (4), and then
at least two successive zone groups (72) each comprising:
a release zone (6), and
at least one capture zone (52), complementary to said related release zone (6).

9. Device for determination according to claim 5, characterized in that the capillary diffusion means (2) includes:
the upstream release zone (4),
one or two upstream capture zone(s) (51), complementary to said upstream release zone (4), and then
a downstream release zone (6), and
at least two second capture zones (52), complementary to said downstream release zone (6).

10. Device for determination according to claim 5, characterized in that the capillary diffusion means (2) includes:
the upstream release zone (4),
one or two upstream capture zone(s) (51), complementary to said upstream release zone (4), and then
at least two successive zone groups (72) each comprising:
a release zone (6), and
at least one capture zone (52), complementary to said related release zone (6).

11. Device for determination according to claim 1, for the detection of at least two analytes, characterized in that the detection reagent of a release zone (4, 6) and/or the capture reagent of the complementary capture zone(s), immediately downstream of said release zone (4, 6), are capable of specifically binding to one of said analytes.

12. Device for determination according to claim 1, characterized in that the number of downstream release zone(s) (6) materialized on the capillary diffusion means (2), each inserted between two capture zones (5), is from 1 to 4.

13. Device for determination according to claim 1, characterized in that the number of capture zone(s) (5) materialized on the capillary diffusion mean (2), complementary to one of the release zones (4, 6) located directly upstream, is from 1 to 10.

14. Device for determination according to claim 1, characterized in that the detection reagent of a release zone (4, 6) and the capture reagent of the complementary capture zone (5) or of at least one of them are capable of specifically binding to the analyte or at least one of the analytes to constitute a sandwich format test.

15. Device for determination according to claim 1, characterized in that the detection reagent of at least one of the release zones (4, 6) and the capture reagent of the complementary capture zone (5) or at least one of them consist, in one case, in an analogue of the analyte to be determined and, in the other case, in a reagent capable of specifically binding to said analyte or to said analogue of the analyte, to constitute a competition format test.

16. Process for the quantitative determination of an analyte in a liquid sample deposited on a device for determination according to claim 1, characterized in that it comprises the following successive steps:
- a step of measuring the signal strength at each capture zone (51, 52),
- in each zone group (7), a step of adding said measured strengths,
- a step of calculating a strength ratio corresponding to the added strengths for one zone group relative to the added strengths for another zone group, and
- a step of associating said calculated strength ratio to a quantitative value of the analyte in said liquid sample from a standard curve corresponding to the strength ratio calculated on the basis of an analyte amount in said liquid sample.

* * * * *